(12) United States Patent
Bathe et al.

(10) Patent No.: US 7,132,272 B2
(45) Date of Patent: Nov. 7, 2006

(54) NUCLEOTIDE SEQUENCE ENCODING CORYNEBACTERIUM GLUTAMICUM LEUCINE RESPONSE REGULATORY PROTEIN

(75) Inventors: Brigitte Bathe, Salzkotten (DE); Jörn Kalinowski, Bielefeld (DE); Alfred Pühler, Bielefeld (DE); Bettina Möckel, Bielefeld (DE); Walter Pfefferle, Halle (DE)

(73) Assignee: Degussa AG, Dusseldorf (DE)

( * ) Notice: Subject to any disclaimer, the term of this patent is extended or adjusted under 35 U.S.C. 154(b) by 469 days.

(21) Appl. No.: 10/134,640

(22) Filed: Apr. 30, 2002

(65) Prior Publication Data

US 2003/0017555 A1    Jan. 23, 2003

Related U.S. Application Data

(63) Continuation-in-part of application No. 09/456,304, filed on Dec. 8, 1999, now abandoned.

(30) Foreign Application Priority Data

Oct. 5, 1999    (DE)    ................ 199 47 792

(51) Int. Cl.
  C12N 1/20    (2006.01)
  C12N 15/09   (2006.01)
  C07H 21/04   (2006.01)
(52) U.S. Cl. .................. 435/252.3; 435/252.33; 435/320.1; 536/23.7; 536/24.32; 536/24.3
(58) Field of Classification Search .......... 536/23.7, 536/24.32; 435/320.1, 252.3
See application file for complete search history.

(56) References Cited

U.S. PATENT DOCUMENTS

2005/0153402 A1*   7/2005   Pompejus et al. .......... 435/106

FOREIGN PATENT DOCUMENTS

EP    0 197 335    10/1986
WO    WO 99/18228    4/1999

OTHER PUBLICATIONS

Voet et al. "Biochemistry, 2nd Ed." Wiley and Sons, Inc. New York, 1995, p. 966.*

Branden et al. "Introduction to Protein Structure". Garland Publishing Inc., New York, 1991, p. 247.*
Witkowski et al. (1999) Biochemistry 38:11643-11650.*
Database GenBank Accession No. B60643, Jun. 1998.*
King and O'Brian, "Identification of Irp gene in Bradyrhizobium japonicum and its role in regulation of δ-aminolevulinic acid uptake", Journal of Bacteriology, vol. 179, No. 5, p. 1828-1831, 1997.
Janes et al., "Two roles for the leucine-responsive regulatory protein in expression of the alanine catabolic operon (dadAB) in Klebsiella aerogenes". Journal of Bacteriology, vol. 181, No. 3, p. 1054-1058, 1999.
Charlier et al., "Cloning and identification of the Sulfolobus solfataricus Irp gene encoding an archaeal homologue of the eurobacterial leucine-responsive global transcriptional regulator Lrp.", Gene, 201, p. 63-68, 1997.
Belitsky et al., "An Irp-like gene of Bacillus subtilis involved in branched-chain amino acid transport". Journal of Bacteriology, vol. 179, No. 17, p. 5448-5457, 1997.
Schrumpf et al., "Isolation and prominent characteristics of an L-lysine hyperproducing strain of Corynebacterum glutamicum.", Applied Microbiology and Biotechnology, vol. 37, p. 566-571, 1992.
Patek et al., "Leucine synthesis in Corynebacterium glutamicum: enzyme activities, structure of leuA, and effect of leuA inactivation of lysine synthesis.", Applied and Environmental Microbiology, vol. 60, No. 1, p. 133-140, 1994.
Changfeng et al., "Comparison of the sensitivities of two Escherichia coli genes to in vivo variation of Lrp concentration." Journal of Bacteriology, Feb. 1998. pp. 655-659.
Calvo et al., "The leucine-responsive regulatory protein, a global regulator of metabolism in Escherichia coli," Microbiological Reviews, vol. 58, Nr.3, 1994, pp. 466-490.
Database EMBL, Accession Y10417, Apr. 1, 1997, Hay N.A. et al., XP002159022.
Database EMBL, Accession P37424, Oct. 1, 1994, Freidberg et al., XP002159024.

* cited by examiner

*Primary Examiner*—David J. Steadman
(74) *Attorney, Agent, or Firm*—Pillsbury Winthrop Shaw Pittman LLP (57) ABSTRACT

The present invention relates to an isolated polynucleotide coding for the lrp gene and to a process for the fermentative production of L-amino acids by altering the expression of this gene.

4 Claims, 1 Drawing Sheet

NUCLEOTIDE SEQUENCE ENCODING CORYNEBACTERIUM GLUTAMICUM LEUCINE RESPONSE REGULATORY PROTEIN

CROSS REFERENCE TO RELATED APPLICATIONS

The present application is a continuation-in-part of U.S. Ser. No. 09/456,304, filed on Dec. 8, 1999, now abandoned, and claims priority to German application DE 199 47 792.2, filed on Oct. 5, 1999.

FIELD OF THE INVENTION

The present invention provides nucleotide sequences coding for the lrp gene and a process for the fermentative production of amino acids, in particular lysine and isoleucine, using coryneform bacteria in which expression of the lrp gene is modified.

BACKGROUND OF THE INVENTION

L-amino acids are used in animal nutrition, in the food industry, in human medicine and in the pharmaceuticals industry. It is known that these amino acids are produced by fermentation of strains of coryneform bacteria in particular *Corynebacterium glutamicum*. Due to their great significance, efforts are constantly being made to improve the production process. Improvements to the process may relate to measures concerning fermentation technology, for example stirring and oxygen supply, or to the composition of the nutrient media, such as for example sugar concentration during fermentation, or to working up of the product by, for example, ion exchange chromatography, or to the intrinsic performance characteristics of the microorganism itself.

The performance characteristics of these microorganisms are improved using methods of mutagenesis, selection and mutant selection. In this manner, strains are obtained which are resistant to antimetabolites, such as for example the lysine analogue S-(2-aminoethyl)cysteine, or are auxotrophic for regulatorily significant amino acids and produce L-amino acids. For some years, the methods of recombinant DNA technology have also been used for strain improvement of strains of *Corynebacterium* which produce L-amino acid.

LRP (leucine-responsive protein) is a global regulator, first described in *Escherichia coli*, which influences the transcription of a series of genes, the gene products of which are involved in the transport, biosynthesis and degradation of amino acids (Calvo et al, *Microbiol. Rev.* 58:466–490 (1994)). In recent years, similar genes have also been identified in other organisms, such as *Bradyrhizobium japonicum* (King, et al., *J. Bacteriol.* 179:1828–1831 (1997)), *Klebsiella aerogenes* (Janes, et al, *J. Bacteriol.* 181:1054–1058 (1999)), *Sulfolobus acidocaldarius* (Charlier et al., *Gene* 201:63–68 (1997)) and in the gram positive bacterium *Bacillus subtilis* (Belitsky, et al., *J. Bacteriol.* 179:5448–5457 (1997)).

In *E. coli*, the lrp protein regulates its own expression. Lrp also has an either negative or positive influence on many genes in *E. coli*. In general, it is the expression of gene products which are active in biosynthetic pathways which is stimulated. Gene products having a catabolic action are generally correspondingly negatively controlled. In some cases, the action of lrp is potentiated by the addition of L-leucine, but addition of L-leucine may also have a negative effect (Newman, et al., In: Neidhardt et al. *Escherichia coli and Salmonella typhimurium: Cellular and molecular biology*, American Society for Microbiology, Washington D.C., pp. 1513–1525 (1996)). In *E. coli*, lrp regulates a large number of genes and operons which play a central role in amino acid biosynthesis and amino acid catabolism. The following operons in *E. coli* are, for example, negatively controlled: livJ, which codes for a binding protein in a highly sophisticated uptake system for branched-chain amino acids (Haney, et al., *J. Bacteriol.* 174:108–115 (1992)) and lysU, which codes for lysine tRNA synthetase (Gazeau, et al., *FEBS Letters* 300:254–258 (1994)). Genes which have hitherto been known to be positively influenced in *E. coli* include, inter alia, ilvIH, gltBDF and leuABCD (Lin, et al., *J. Bacteriol.* 174:1948–1955 (1992)).

The last-stated operon is of fundamental interest in leucine biosynthesis and of particular interest for lysine biosynthesis in *Corynebacterium glutamicum*. It is suspected that there is an association between leucine auxotrophy and elevated lysine productivity values (Schrumpf et al. *Appl. Microbiol. Biotech.* 37:566–571 (1992)). Patek, et al. (*Appl. Environ. Microbiol.* 60:133–140 (1994)) have demonstrated that inactivating leuA in some lysine producers of *C. glutamicum* results in increased lysine yields. In a mutant of *Brevibacterium lactofermentum*, Tosaka, et al. (*Agri. Biol. Chem.* 43:265–270 (1979)) have been able to achieve a reduction in lysine formation with a simultaneous increase in threonine formation by addition of L-leucine.

OBJECT OF THE INVENTION

The inventors set themselves the object of providing novel measures for the improved fermentative production of L-amino acids, in particular L-lysine and L-isoleucine, with coryneform bacteria.

SUMMARY OF THE INVENTION

The present invention provides an isolated polynucleotide from coryneform bacteria containing a polynucleotide sequence selected from the group:
  a) polynucleotide which is at least 70% identical to a polynucleotide which codes for a polypeptide containing the amino acid sequence of SEQ ID NO:2,
  b) polynucleotide which codes for a polypeptide which contains an amino acid sequence which is at least 70% identical to the amino acid sequence of SEQ ID NO:2,
  c) polynucleotide which is complementary to the polynucleotides of a) or b) and
  d) polynucleotide containing at least 15 successive bases of the polynucleotide sequence of a), b) or c).

The present invention also provides the polynucleotide according to claim 1, wherein it preferably comprises a replicable DNA containing:
  (i) the nucleotide sequence shown in SEQ ID NO:1, or
  (ii) at least one sequence which matches the sequence (i) within the degeneration range of the genetic code, or
  (iii) at least one sequence which hybridizes with the sequence complementary to sequence i) or (ii) and optionally
  (iv) functionally neutral sense mutations in (i).

The present invention also provides a polynucleotide according to claim 2, containing the nucleotide sequence as shown in SEQ ID NO:1, and a polynucleotide according to claim 2 which codes for a polypeptide which contains the amino acid sequence as shown in SEQ ID NO:2.

The present invention also provides polynucleotides which substantially consist of one polynucleotide sequence and are obtainable by hybridization screening of an appropriate gene library which contains the complete gene having the polynucleotide sequence corresponding to SEQ ID NO:1 with a probe which contains the sequence of the stated polynucleotide according to SEQ ID NO:1 or a fragment thereof and isolation of the stated DNA sequence.

BRIEF DESCRIPTION OF THE DRAWINGS

FIG. 1.

DETAILED DESCRIPTION OF THE INVENTION

Polynucleotide sequences according to the invention are suitable as hybridization probes for RNA, cDNA and DNA in order to isolate full length cDNA which code for the lrp protein and to isolate such cDNA or genes, the sequence of which exhibits a high level of similarity with that of the lrp gene. Polynucleotide sequences according to the invention are furthermore suitable as primers for the production of DNA of genes which code for lrp proteins by the polymerase chain reaction (PCR). Such oligonucleotides acting as probes or primers contain at least 30, preferably at least 20, very particularly preferably at least 15 successive bases. Oligonucleotides having a length of at least 40, 50, 60, 70, 80, 90 nucleotides are also suitable. Oligonucleotides with a length of at least 100, 150, 200, 250 or 300 nucleotides are optionally also suitable.

"Isolated" means separated from its natural surroundings.

"Polynucleotide" generally denotes polyribonucleotides and polydeoxyribonucleotides, wherein the RNA or DNA may be unmodified or modified.

"Polypeptides" is taken to mean peptides or proteins which contain two or more amino acids joined via peptide bonds.

The polypeptides according to the invention include a polypeptide according to SEQ ID NO:2, in particular those having the biological activity of the lrp protein and also those which are at least 70%, preferably at least 80%, identical to the polypeptide according to SEQ ID NO:2 and in particular which exhibit 90% to 95% identity to the polypeptide according to SEQ ID NO:2 and exhibit the stated activity.

The invention furthermore relates to a process for the fermentative production of amino acids, in particular L-lysine and L-isoleucine by means of coryneform bacteria, which in particular already produce amino acids, by amplifying or attenuating the novel lrp gene as a function of the target substance. In this connection, the term "amplification" describes the increase in the intracellular activity or concentration of one or more proteins or enzymes respectively in a microorganism, which proteins are coded by the corresponding DNA, for example by increasing the copy number of the gene or genes, by using a strong promoter or a gene or allele which codes for a corresponding protein having elevated activity and optionally by combining these measures. By amplification measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism. In this connection, the term "attenuation" means reducing or suppressing the intracellular activity or concentration of one or more proteins or enzymes respectively in a microorganism, which enzymes are coded by the corresponding DNA, for example by using a weak promoter or a gene or allele which codes for a corresponding protein which has a low activity or inactivates the corresponding protein and optionally by combining these measures.

By attenuation measures, the activity or concentration of the corresponding protein is in general reduced to 0 to 75%, 0 to 50%, 0 to 25%, 0 to 10% or 0 to 5% activity or concentration of the wild-type protein or of the activity or concentration of the protein in the starting microorganism.

The microorganisms, provided by the present invention, may produce L-lysine from glucose, sucrose, lactose, fructose, maltose, molasses, starch, cellulose or from glycerol and ethanol. They may comprise representatives of coryneform bacteria, in particular of the genus *Corynebacterium*. Within the genus *Corynebacterium*, *Corynebacterium glutamicum* may in particular be mentioned, which is known in specialist circles for its ability to produce L-amino acids. Suitable strains of the genus *Corynebacterium*, in particular of the species *Corynebacterium glutamicum*, are for example the known wild type strains.

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 and amino acid producing mutants or strains produced therefrom, such as for example the L-lysine producing strains

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464 and
*Corynebacterium glutamicum* DSM5715 or the L-isoleucine producing strains

*Corynebacterium glutamicum* ATCC14309
*Corynebacterium glutamicum* ATCC14310
*Corynebacterium glutamicum* ATCC14311
*Corynebacterium glutamicum* ATCC15168 and
*Corynebacterium ammoniagenes* ATCC6871.

The inventors succeeded in isolating the novel lrp gene which codes for the lrp protein from *C. glutamicum*. The gene or also other genes are isolated from *C. glutamicum* by initially constructing a gene library of this microorganism in *E. coli*. The construction of gene libraries is described in generally known textbooks and manuals. Examples which may be mentioned are the textbook by Winnacker, Gene und Klone, *Eine Einführung in die Gentechnologie* (Verlag Chemie, Weinheim, Deutschland, 1990) or the manual by Sambrook et al.: *Molecular Cloning, A Laboratory Manual* (Cold Spring Harbor Laboratory Press, 1989). One very well known gene library is that of *E. coli* K-12 strain W3110, which was constructed by Kohara et al. (*Cell* 50:495–508 (1987)) in λ-vectors. Bathe et al. (*Mol. Gen. Genet.* 252: 255–265 (1996)) describe a gene library of *C. glutamicum* ATCC13032, which was constructed using the cosmid vector SuperCos I (Wahl, et al., *Proc. Nat'l Acad. Sci. USA* 84:2160–2164 (1987)) in *E. coli* K-12 strain NM554 (Raleigh, et al., *Nucl. Ac. Res.* 16:1563–1575 (1988)). Bathe, et al. (*Mol. Gen. Genet.* 6:3–317, 326) also describe a gene library of *C. glutamicum* ATCC13032, using cosmid pHC79 (Hohn, et al. *Gene* 11:291–298 (1980)). Plasmids such as pBR322 (Bolivar, *Life Sci.* 25:807–818 (1979)) or pUC9 (Viera, et al., Gene 19:259–268 (1982)) may also be used to produce a gene library of *C. glutamicum* in *E. coli*. Particularly suitable hosts are those strains of *E. coli* which exhibit defects with regard to restriction and recombination. One example of such a strain is the strain DH5αmcr, which has been described by Grant et al. (*Proc. Nat'l Acad. Sci. USA* 87:4645–4649 (1990)). The long DNA fragments cloned with the assistance of cosmids may then in turn be subcloned in vectors suitable for sequencing and then be sequenced, as described, for example, in Sanger et al. (*Proc. Nat'l Acad. Sci. USA* 74:5463–5467 (1977)). The novel DNA sequence from *C. glutamicum* which codes for the lrp gene and, as shon in SEQ ID NO:1, was obtained in this manner. The amino acid sequence of the corresponding protein was furthermore deduced from the above DNA sequence using the methods described above. The resultant amino acid sequence of the lrp gene product is shown in SEQ ID NO:2.

Coding DNA sequences arising from the degeneracy of the genetic code are also provided by the present invention. DNA sequences which hybridize with SEQ ID NO:1 or parts of SEQ ID NO:1 are similarly also provided by the invention. Conservative substitutions of amino acids in proteins, for example the substitution of glycine for alanine or of aspartic acid for glutamic acid, are known in specialist circles as "sense mutations", which result in no fundamental change in activity of the protein, i.e. they are functionally neutral. It is furthermore known that changes to the N and/or C terminus of a protein do not substantially impair or may even stabilize the function thereof. The person skilled in the art will find information in this connection inter alia in Ben-Bassat et al. (*J. Bacteriol* 169:751–757 (1987)), in O'Regan et al. (*Gene* 77:237–251 (1989)), in Sahin-Toth et al. (*Prot. Sci.* 3:240–247 (1994)), in Hochuli et al. (*Bio/Technology* 6:1321–1325 (1988)) and in known textbooks of genetics and molecular biology. Amino acid sequences arising in a corresponding manner from SEQ ID NO:2 are also provided by the present invention.

DNA sequences which hybridize with SEQ ID NO:1 or parts of SEQ ID NO:1 are also provided by the invention. Finally, DNA sequences produced by the polymerase chain reaction (PCR) using primers obtained from SEQ ID NO:1 are also provided by the present invention. Such oligonucleotides typically have a length of at least 15 base pairs. The person skilled in the art will find instructions for identifying DNA sequences by means of hybridization inter alia in the manual "The DIG System Users Guide for Filter Hybridization" from Boehringer Mannheim GmbH (Mannheim, Germany, 1993) and in Liebl et al. (*Internat'l J. Systemat. Bacteriol.* 41:255–260 (1991)). The person skilled in the art will find instructions for amplifying DNA sequences by means of the polymerase chain reaction (PCR) inter alia in the textbook by Gait, *Oligonucleotide synthesis: a practical approach* (IRL Press, Oxford, UK, 1984) and in Newton and Graham, *PCR* (Spektrum Akademischer Verlag, Heidelberg, Deutschland, 1994).

The inventors discovered that the lrp gene is important for the production of amino acids, in particular L-lysine and L-isoleucine. In particular, it has been found that L-lysine production by coryneform bacteria can be improved by attenuation of the lrp gene. To achieve an attenuation, either the expression of the lrp gene or the catalytic/regulatory properties of the enzyme protein can be reduced or eliminated. The two measures can optionally be combined.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this, e.g., in the patent application WO 96/15246, in Boyd, et al., (*J. Bacteriol.* 170:5949 (1988)), in Voskuil et al., (*Nucl. Ac. Res.* 26:3548 (1998)), in Jensen et al. (*Biotech. Bioeng.* 58:191 (1998)), in Pátek, et al. (*Microbiol.* 142:1297 (1996)), Vasicova, et al. (*J. Bacteriol.* 181: 6188 (1999)) and in known textbooks of genetics and molecular biology, such as, e.g., the textbook by Knippers (*Molekulare Genetik,* 6th edition, Georg Thieme Verlag, Stuttgart, Germany, 1995) or that by Winnacker (*Gene und Klone,* VCH Verlagsgesellschaft, Weinheim, Germany, 1990).

Mutations which lead to a change or reduction in the catalytic properties of enzyme proteins are known from the prior art; examples which may be mentioned are the works by Qiu, et al (*J. Biol. Chem.* 272:8611–8617 (1997)), Sugimoto, et al(*Biosci. Biotech. Biochem.* 61:1760–1762 (1997)) and Möckel (*Die Threonindehydratase aus Corynebacterium glutamicum: Aufhebung der allosterischen Regulation und Struktur des Enzyms,* Reports from the Jülich Research Center, Jül-2906, ISSN09442952, Jülich, Germany, 1994). Summarizing descriptions can be found in known textbooks of genetics and molecular biology, such as, e.g. that by Hagemann (*Allgemeine Genetik,* Gustav Fischer Verlag, Stuttgart, 1986). Possible mutations are transitions, transversions, insertions and deletions. Depending on the effect of the amino acid exchange on the enzyme activity, "missense mutations" or "nonsense mutations" are referred to. Insertions or deletions of at least one base pair (bp) in a gene lead to frame shift mutations, as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e.g. the textbook by Knippers (*Molekulare Genetik,* 6th edition, Georg Thieme Verlag, Stuttgart, Germany, 1995), that by Winnacker (*Gene und Klone,* VCH Verlagsgesellschaft, Weinheim, Germany, 1990) or that by Hagemann (*Allgemeine Genetik,* Gustav Fischer Verlag, Stuttgart, 1986).

A common method of mutating genes of *C. glutamicum* is the method of "gene disruption" and "gene replacement" described by Schwarzer, et al. (*Bio/Technology* 9:84–87 (1991)). In the method of gene disruption a central part of the coding region of the gene of interest is cloned in a plasmid vector which can replicate in a host (typically *E. coli*), but not in *C. glutamicum*. Possible vectors are, for example, pSUP301 (Simon, et al., *Bio/Technology* 1:784–791 (1983)), pK18mob or pK19mob (Schäfer, et al., *Gene* 145:69–73 (1994)), pK18mobsacB or pK19mobsacB (Jäger, et al., *J. Bacteriol.* 174:5462–65 (1992)), pGEM-T (Promega Corporation, Madison, Wis., USA), pCR2.1-TOPO (Shuman, *J. Biol. Chem.* 269:32678–84 (1994); U.S. Pat. No. 5,487,993); pCR®Blunt Invitrogen, Groningen, Holland; Bernard et al., *J. Mol. Biol.* 234:534–541 (1993)) or pEM1 (Schrumpf, et al., *J. Bacteriol.* 173:4510–4516 (1991)). The plasmid vector which contains the central part of the coding region of the gene is then transferred into the desired strain of *C. glutamicum* by conjugation or transformation. The method of conjugation is described, for example, by Schäfer et al (*Appl. Environ. Microbiol* 60:756–759 (1994)). Methods for transformation are described, for example, by Thierbach, et al. (*Appl. Microbiol. Biotechnol.* 29:356–362 (1988)), Dunican, et al. (*Bio/Technology* 7:1067–1070 (1989)) and Tauc et al. (*FEMS Microbiol. Lett.* 123:343–347 (1994)). After homologous recombination by means of a "cross-over" event, the coding region of the gene in question is interrupted by the vector sequence and two incomplete alleles are obtained, one lacking the 3' end and one lacking the 5' end. This method has been used, for example, by Fitzpatrick, et al. (*Appl. Microbiol. Biotechnol* 42:575–580 (1994)) to eliminate the recA gene of *C. glutamicum*.

In the method of "gene replacement", a mutation, such as e.g., a deletion, insertion or base exchange, is established in vitro in the gene of interest. The allele prepared is in turn cloned in a vector which is not replicative for *C. glutamicum* and this is then transferred into the desired host of *C. glutamicum* by transformation or conjugation. After homologous recombination by means of a first "cross-over" event which effects integration and a suitable second "cross-over" event which effects excision in the target gene or in the target sequence, the incorporation of the mutation or of the allele is achieved. This method was used, for example, by Peters-Wendisch, et al. (*Microbiol.* 144:915–927 (1998)) to eliminate the pyc gene of *C. glutamicum* by a deletion. A deletion, insertion or a base exchange can be incorporated into the lrp gene in this manner.

The inventors furthermore discovered that the additional overexpression of one or more enzymes of the particular biosynthetic pathway, of glycolysis, of the citric acid cycle, of anaplerotic metabolism or of amino acid export, individually or in combination, results in further advantages for the production of amino acids, in particular L-lysine and L-isoleucine. Thus, for example, for the production of L-lysine:

the dap A gene (EP-B 0 197 335) which codes for dihydropicolinate synthase may simultaneously be overexpressed, or the gap gene (Schwinde et al., Journal of Bacteriology 175:3905–3908 (1993)) which codes for glyceraldehyde 3-phosphate dehydrogenase may simultaneously be overexpressed, or the mqo gene (Molenaar et al., European Journal of Biochemistry 254, 395–403 (1998)) (SEQ ID NOS: 10 and 11) which codes for malae:quinone oxidoreductase may simultaneously be overexpressed, or the pyc gene (DE-A-19 831 609) (SEQ ID NOS: 12 and 13) which codes for pyruvate carboxylase may simultaneously be overexpressed, or the lysE gene (DE-A-195 48 222) which codes for lysine export may simultaneously be overexpressed.

Thus, for example, for the production of L-isoleucine the ilvA gene (Möckel et al., Journal of Bacteriology (1992)8065–8072)) which codes for threonine dehydratase or the "feed back resistant" ilvA(Fbr) allele (Möckel et al., (1994) Molecular Microbiology 13: 833–842) may simultaneously be overexpressed, or the gap gene (Schwinde et al., Journal of Bacteriology 175: 3905–3908 (1993)) which codes for glyceraldehyde 3-phosphate dehydrogenase may simultaneously be overexpressed, or the mqo gene (Molenaar et al., European Journal of Biochemistry 254, 395–403 (1998)) which codes for malate:quinone oxidoreductase may simultaneously be overexpressed, or the pyc gene (DE-A-19 831 609) which codes for pyruvate carboxylase may simultaneously be overexpressed.

The use of endogenous genes is preferred. "Endogenous genes" or "endogenous nucleotide sequences" refer to genes or nucleotide sequences which are available in the population of a species.

In may furthermore be advantageous for the production of amino acids, in particular L-lysine and L-isoleucine, to suppress unwanted secondary reactions (Nakayama: "Breeding of Amino Acid Producing Micro-organisms," in: *Overproduction of Microbial Products*, Krumphanzl, Sikyta, Vanek (eds.), Academic Press, London, UK, 1982).

For the purposes of amino acid production, in particular of L-lysine and L-isoleucine, the microorganisms produced according to the invention may be cultured continuously or discontinuously using the batch process or the fed batch process or repeated fed batch process. A summary of known culture methods is given in the textbook by Chmiel (*Bioprozesstechnik* 1. *Einführung in die Bioverfahrenstechnik*, Gustav Fischer Verlag, Stuttgart, 1991) or in the textbook by Storhas (*Bioreaktoren und periphere Einrichtungen*, Vieweg Verlag, Braunschweig/Wiesbaden, 1994)). The culture medium to be used must adequately satisfy the requirements of the particular strains. Culture media for various microorganisms are described in "Manual of Methods for General Bacteriology" from American Society for Bacteriology (Washington D.C., USA, 1981). Carbon sources which may be used include sugars and carbohydrates, such as for example glucose, sucrose, lactose, fructose, maltose, molasses, starch and cellulose, oils and fats, such as for example soya oil, sunflower oil, peanut oil and coconut oil, fatty acids, such as for example palmitic acid, stearic acid and linoleic acid, alcohols, such as for example glycerol and ethanol, and organic acids, such as for example acetic acid. These substances may be used individually or as a mixture.

Nitrogen sources which may be used comprise organic compounds containing nitrogen, such as peptones, yeast extract, meat extract, malt extract, corn steep liquor, soya flour and urea or inorganic compounds, such as ammonium sulfate, ammonium chloride, ammonium phosphate, ammonium carbonate and ammonium nitrate. The nitrogen sources may be used individually or as a mixture.

Phosphorus sources which may be used comprise phosphoric acid, potassium dihydrogen phosphate or dipotassium hydrogen phosphate or the corresponding salts containing sodium. The culture medium must furthermore contain salts of metals, such as for example magnesium sulfate or iron sulfate, which are required for growth. Finally, essential growth-promoting substances such as amino acids and vitamins may also be used in addition to the above-stated substances. In addition, suitable precursors may be added to the culture medium. The stated materials may be added to the culture in the form of a single batch or may be supplied in a suitable manner during culturing.

The pH of the culture is controlled by using basic compounds such as sodium hydroxide, potassium hydroxide, ammonia or ammonia solution or acidic compounds such as phosphoric acid or sulfuric acid in a suitable manner. Antifoaming agents, such as for example fatty acid polyglycol esters, may be used to control foaming. Suitable, selectively acting substances, for example antibiotics, may be added to the medium in order to maintain plasmid stability. Oxygen or gas mixtures containing oxygen, such as for example air, are introduced into the culture in order to maintain aerobic conditions. The temperature of the culture is normally from 20° C. to 45° C. and preferably from 25° C. to 40° C. The culture is continued until the maximum quantity of the desired amino acid has formed. This objective is normally achieved within 10 hours to 160 hours.

The amino acids may be analyzed by anion exchange chromatography with subsequent ninhydrin derivation, as described in Spackman, et al. (*Analyt. Chem.* 30:1190 (1958)) or by reversed phase HPLC, as described in Lindroth, et al. (*Analyt. Chem.* 51:1167–1174 (1979)).

The following microorganism was deposited on Aug. 29th 2000 as a pure culture at the Deutsche Sammlung für Mikroorganismen und Zellkulturen (DSMZ=German Collection of Microorganisms and Cell Cultures, Braunschweig, Germany) in accordance with the Budapest Treaty: *E. coli* S17-1/pK19mobsacBΔlrp as DSM 13702.

The purpose of the process according to the invention is the fermentative production of amino acids, in particular L-lysine and L-isoleucine. The present invention is illustrated in greater detail by the following examples.

EXAMPLES

Example 1

Production of a Genomic Cosmid Gene Library from *Corynebacterium glutamicum* ATCC13032

Chromosomal DNA from *Corynebacterium glutamicum* ATCC13032 was isolated as described in Tauch et al. (*Plasmid* 33:168–179 (1995)) and partially cleaved with the restriction enzyme Sau3AI (Amersham Pharmacia, Freiburg, Germany, product description Sau3AI, code no. 27-0913-02). The DNA fragments were dephosphorylated with shrimp alkaline phosphatase (Roche Molecular Biochemicals, Mannheim, Germany, production description SAP, code no. 1758250). The DNA of cosmid vector SuperCos1 (Wahl, et al., *Proc. Nat'l Acad. Sci. USA* 84:2160–2164 (1987)), purchased from Stratagene (La Jolla, USA, production description SuperCos1 Cosmid Vector Kit, code no. 251301) was cleaved with the restriction enzyme XbaI (Amersham Pharmacia, Freiburg, Germany, product description XbaI, Code no. 27-0948-02) and also dephosphorylated with shrimp alkaline phosphatase. The cosmid DNA was then cleaved with the restriction enzyme BamHI (Amersham Pharmacia, Freiburg, Germany, product description BamHI, code no. 27-0868-04). Cosmid DNA treated in this manner was mixed with the treated ATCC 13032 DNA and the batch was treated with T4 DNA ligase (Amersham Pharmacia, Freiburg, Germany, product description T4 DNA Ligase, code no. 27-0870-04). The ligation mixture was then packed in phages using Gigapack II XL Packing Extracts (Stratagene, La Jolla, USA, product description Gigapack II XL Packing Extract, code no. 200217). *E. coli* strain NM554 (Raleigh et al. 1988, Nucleic Acid Res. 16:1563–1575) was infected by suspending the cells in 10 mM $MgSO_4$ and mixing them with an aliquot of the phage suspension. The cosmid library was infected and titred as described in Sambrook, et al (*Molecular Cloning: A Laboratory Manual*, Cold Spring Harbor (1989)), wherein the cells were plated out on LB agar (Lennox, *Virology* 1:190 (1955) +100 µg/ml of ampicillin. After overnight incubation at 37° C., individual recombinant clones were selected.

Example 2

Isolation and Sequencing of the lrp Gene

Cosmid DNA from an individual colony was isolated in accordance with the manufacturer's instructions using the Qiaprep Spin Miniprep Kit (Product No. 27106, Qiagen, Hilden, Germany) and partially cleaved with the restriction enzyme Sau3AI (Amersham Pharmacia, Freiburg, Germany, product description Sau3AI, code no. 27-0913-02). The DNA fragments were dephosphorylated with shrimp alkaline phosphatase (Roche Molecular Biochemicals, Mannheim, Germany, production description SAP, code no. 1758250). Once separated by gel electrophoresis, the cosmid fragments of a size of approx. 1500 to 2000 bp were isolated using the QiaExII Gel Extraction Kit (product no. 20021, Qiagen, Hilden, Germany). The DNA of the sequencing vector pZero-1 purchased from Invitrogen (Groningen, Netherlands, product description Zero Background Cloning Kit, product no. K2500-01) was cleaved with the restriction enzyme BamHI (Amersham Pharmacia, Freiburg, Deutschland, product description BamHI, Product No. 27-0868-04). Ligation of the cosmid fragments into the sequencing vector pZero-1 was performed as described by Sambrook et al. (*Molecular Cloning: A Laboratory Manual*, Cold Spring Harbor (1989)), wherein the DNA mixture was incubated overnight with T4 ligase (Pharmacia Biotech, Freiburg, Germany).

This ligation mixture was then electroporated into the *E. coli* strain DH5αMCR (Grant, *Proc. Nat'l Acad. Sci. USA* 87:4645–4649 (1990); Tauch, et al., *FEMS Microbiol. Lett.* 123:343–7 (1994)) and plated out onto LB agar (Lennox, *Virol.* 1:190 (1955)) +50 µg/ml of Zeocin. Plasmids of the recombinant clones were prepared using the Biorobot 9600 (product no. 900200, Qiagen, Hilden, Germany). Sequencing was performed using the dideoxy chain termination method according to Sanger, et al. (*Proc. Nat'l Acad. Sci. USA* 74:5463–5467 (1977)) as modified by Zimmermann, et al. (*Nucl. Ac. Res.* 18:1067 (1990)). The "RR dRhodamin Terminator Cycle Sequencing Kit" from PE Applied Biosystems (product no. 403044, Weiterstadt, Germany) was used. Separation by gel electrophoresis and analysis of the sequencing reaction was performed in a "Rotiphorese NF" acrylamide/bisacrylamide gel (29:1) (product no. A124.1, Roth, Karlsruhe, Germany) using the "ABI Prism 377" sequencer from PE Applied Biosystems (Weiterstadt, Germany).

The resultant raw sequence data were then processed using the Staden software package (*Nucl. Ac. Res.* 14:217–231 (1986)), version 97-0. The individual sequences of the pZero 1 derivatives were assembled into a coherent contig. Computer-aided coding region analysis was performed using XNIP software (Staden, *Nucl. Ac. Res.* 14:217–231 (1986)). Further analysis was performed using the "BLAST search programs" (Altschul, et al., *Nucl. Ac. Res.* 25:3389–3402 (1997)), against the non-redundant NCBI database of the "National Library of Medicine" (USA). The resultant nucleotide sequence is stated in SEQ ID NO:1. Analysis of the nucleotide sequence revealed an open reading frame of 462 base pairs, which was designated the lrp gene. The lrp gene codes for a polypeptide of 154 amino acids and is shown in SEQ ID NO:2.

Example 3

Incorporation of a Deletion into the lrp Gene

Chromosomal DNA was isolated from strain ATCC13032 using the method of Tauch, et al. (*Plasmid* 33:168–179 (1995)). On the basis of the sequence of the lrp gene for *C. glutamicum* known from Example 2, the oligonucleotides described below were selected for producing the lrp deletion allele:

lrp-up-for (see also SEQ ID NO:3):

5'-GGC G(CC CGG G)GG CGT GCG C-3' lrp_up_rev (see also SEQ ID NO:4)

5'-extension-CCC ATC CAC TAA ACT TAA ACA-side-AAT GGA ATC TAG CTT CAT ATA TTG CAC-3' lrp_do_for: (see also SEQ ID NO:5)

5'-extension-TGT TTA AGT TTA GTG GAT GGG-side-GCT ATG AAA GTG GTG AAA CCA GCT-3' lrp-do_rev: (see also SEQ ID NO:6)

5'-CCG G(TC TAG A)GG ATC CGC AAT TCC-3'

The stated primers were synthesized by the company MWG Biotech (Ebersberg, Germany) and the PCR reaction performed using Pfu polymerase (Stratagene, product no. 600135, La Jolla, USA) and the PTC 100 thermal cycler (MJ Research Inc., Waltham, USA). The primers lrp_up_for and lrp_do_rev contain an inserted XmaI (lrp_up_for) or XbaI (lrp_do_rev) restriction site, which are shown above between brackets. The first 397 bp DNA amplification product, designated lrp part 1, was obtained with the oligonucleotides lrp_up_for and lrp_up_rev. It contains the 5' region of the lrp gene (nucleotide 350–376), the "upstream" region of the gene with 349 nucleotides and additionally the 21 bp extension originating from oligonucleotide lrp_up_rev, which extension is complementary to the 5' end of the primer lrp_do_for. The term "side" indicates the separation of the primer "lrp-up-rev" into the artificial region called "5'-extension" and a sequence of the lrp-part 1 region mentioned above. The sequence was checked by sequencing the fragment lrp part 1 using the dideoxy chain termination method, as described by Sanger et al (*Proc. Nat'l Acad. Sci. USA* 74:5463–5467 (1977)). The sequence so determined is shown in SEQ ID NO:7.

The second 402 bp DNA fragment, lrp part 2, was obtained with the oligonucleotides lrp_do_for and lrp_do_rev and comprises the 3' region of the lrp gene (nucleotide 22–60) and 342 bp "downstream" from the gene. This fragment was also sequenced as described in Sanger et al. (*Proc. Nat'l Acad. Sci. USA* 74:5463–5467, (1977)). The sequence so determined is shown in SEQ ID NO:8. The term "side" indicates the separation of the primer "lrp-do-for" into the artificial region called "5'-extension" and a sequence of the lrp-part 2 region mentioned above.

Both PCR products, lrp part 1 and lrp part 2, were used together as a DNA template in a third PCR reaction, wherein due to the overlapping, complementary DNA regions, the "forward" strand of lrp part 1 was able to join with the "reverse" strand of lrp part 2. The extension of this overlapping DNA region or the addition of the oligonucleotides lrp_up_for and lrp_do_rev, results in the production of a 778 bp PCR amplification product, which results in the production of an lrp deletion derivative, as shown in SEQ ID NO:9. The position of the deletion is between nucleotides 376 to 398 of SEQ ID NO:9, where the 21 bp extension originating from oligonucleotides lrp_up_rev and lrp_do_for is located.

Example 4

Incorporation of the Δlrp Allele into the Chromosome

The 778 bp lrp deletion allele obtained in Example 3 was incorporated into the chromosome of *C. glutamicum* by deletion mutagenesis with the assistance of the sacB system described in Schäfer, et al. (*Gene*, 14:69–79 (1994)). This system allows the person skilled in the art to identify or select allele exchanges which are effected by homologous recombination.

4.1 Construction of the Exchange Vector pK19mobsacBΔlrp

The lrp deletion derivative according to SEQ ID NO:9 obtained in Example 3 was cut with the restriction enzymes XmaI and XbaI (Amersham-Pharmacia, Freiburg, Germany), once separated in an agarose gel (0.8%), was isolated from the agarose gel using the Qiagenquick Gel Extraction Kit (Qiagen, Hilden, Germany) and used for ligation with the mobilizable cloning vector pK19mobsacB described in Schäfer, et al. (*Gene* 14:69–73 (1994)). This latter was previously cleaved with the restriction enzymes XmaI and XbaI, mixed with the lrp deletion allele and treated with T4 DNA ligase (Amersham-Pharmacia, Freiburg, Germany).

*E. coli* strain S17-1 (Simon et al., *Bio/Technologie* 1:784–791 (1993)) was then electroporated with the ligation batch (Hanahan, in: *DNA cloning. A practical approach*, vol. 1., ILR-Press, Cold Spring Harbor, N.Y., 1989). The plasmid-bearing cells were selected by plating out the transformation batch onto LB agar (Sambrock, et al, *Molecular Cloning: A Laboratory Manual*, 2$^{nd}$ ed., Cold Spring Harbor, N.Y., 1989), which had been supplemented with 25 mg/l of kanamycin.

Figure 1:
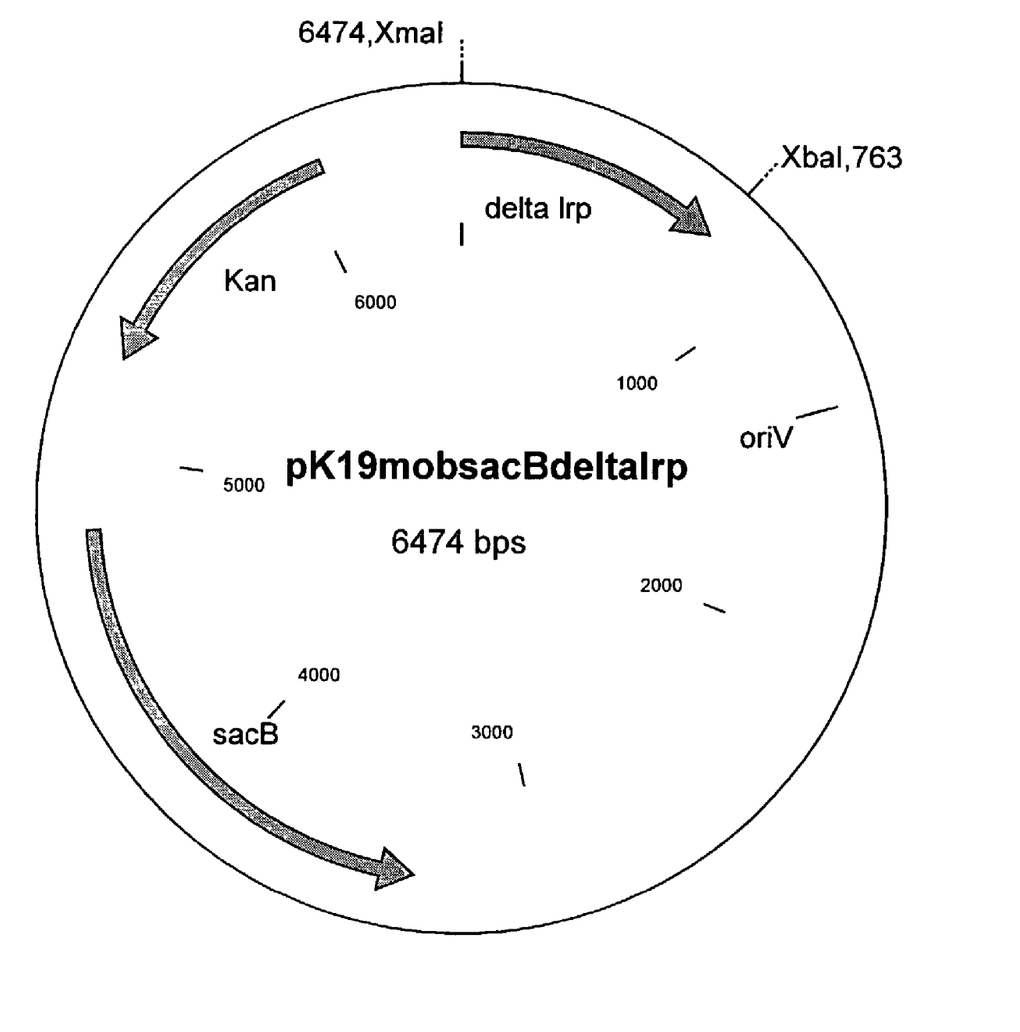
FIG. 1 shows a map of plasmid pK19mobsacBΔlrp (=pK19mobsacB deltalrp).

Plasmid DNA was isolated from a transformant using the QIAprep Spin Miniprep Kit from Qiagen and the cloned lrp deletion allele was verified by means of sequencing by the company MWG Biotech (Ebersberg, Germany). The plasmid was named pK19mobsacBΔlrp and is shown in FIG. 1. The strain *E. coli* S17-1/pK19mobsacBΔlrp containing plasmid pK19mobsacBΔlrp was deposited under number DSM 13702 on Aug. 29, 2000 with Deutsche Sammlung für Mikroorganismen und Zellkulturen (DSMZ, Braunschweig, Germany).

Example 5

Deletion Mutagenesis of the lrp Gene in *C. glutamicum* Strain DSM 5715

The L-lysine producing strain DSM 5715 is described in EP-B-0435132. The vector pK19mobsacBΔlrp stated in Example 4 was electroporated in accordance with the electroporation method of Tauch, et al. (*FEMS Microbiol. Lett.* 123:343–347 (1989)). The vector cannot independently replicate in DSM 5715 and is only retained in the cell if it has been integrated into the chromosome. Clones with integrated pK19mobsacBΔlrp were selected by plating out the electroporation batch onto LB agar (Sambrook, et al., *Molecular Cloning: A Laboratory Manual*, 2$^{nd}$ ed., Cold Spring Harbor, N.Y., 1989), which had been supplemented with 15 mg/l of kanamycin. Clones which had grown were plated onto LB agar plates with 25 mg/l of kanamycin and incubated for 16 hours at 33° C. In order to excise the plasmid together with the complete chromosomal copy of the lrp gene, the clones were then cultured on LB agar with 10% sucrose.

The plasmid pK19mobsacB contains a copy of the sacB gene, which converts sucrose into levansucrase, which is toxic to *C. glutamicum*. Thus, the only clones to grow on LB agar with sucrose are those in which the integrated pK19mobsacBΔlrp has in turn been excised. Excision of the plasmid may be accompanied by the excision of either the complete chromosomal copy of the lrp gene or the incomplete copy with the internal deletion. In order to prove that the incomplete copy of lrp remains in the chromosome, the plasmid pK19mobsacBΔlrp fragment was labeled with the Dig hybridization kit from Boehringer using the method according to "The DIG System Users Guide for Filter Hybridization" from Boehringer Mannheim GmbH (Mannheim, Germany, 1993). Chromosomal DNA of a potential deletion mutant was isolated using the method according to Eikmanns, et al. (*Microbiol* 140:1817–1828 (1994)) and cut into separate batches in each case with the restriction enzymes SphI and PstI. The resultant fragments were separated by agarose gel electrophoresis and hybridized at 68° C. using the Dig hybridization kit from Boehringer. Two hybridizing fragments of approx. 1640 bp and 960 bp were obtained from the control strain, while two hybridizing fragments of approx. 580 bp and 1300 bp were obtained from the mutant. It could thus be shown that strain DSM5715 has lost its complete copy of the lrp gene and, instead, now only has the incomplete copy with the deletion of approx. 380 bp. The strain was designated *C. glutamicum* DSM5715Δlrp.

Example 6

Production of Lysine

The *C. glutamicum* strain DSM5715Δlrp obtained in Example 5 was cultured in a nutrient medium suitable for the production of lysine and the lysine content of the culture supernatant was determined. To this end, the strain was initially incubated for 24 hours at 33° C. on an agar plate. Starting from this agar plate culture, a preculture was inoculated (10 ml of medium in a 100 ml Erlenmeyer flask). The complete medium CgIII was used as the medium for this preculture. The preculture was incubated for 48 hours at 33° C. on a shaker at 240 rpm. A main culture was inoculated from this preculture, such that the initial OD (660 nm) of the main culture was 0.1 OD. Medium MM was used for the main culture.

| Medium MM | |
| --- | --- |
| CSL (Corn Steep Liquor) | 5 g/l |
| MOPS | 20 g/l |
| Glucose (separately autoclaved) | 50 g/l |
| Salts: | |
| $(NH_4)_2SO_4$ | 25 g/l |
| $KH_2PO_4$ | 0.1 g/l |

| -continued | |
| --- | --- |
| Medium MM | |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| $CaCO_3$ | 25 g/l |

CSL, MOPS (N-morpholino-propanesulfonic acid) and the salt solution were adjusted to pH 7 with ammonia water and autoclaved. The sterile substrate and vitamin solutions, together with the dry-autoclaved $CaCO_3$, were then added. Culturing was performed in a volume of 10 ml in a 100 ml Erlenmeyer flask with flow spoilers. Culturing was performed at 33° C. and 80% atmospheric humidity.

After 48 hours, the OD was determined at a measurement wavelength of 660 nm using a Biomek 1000 (Beckmann Instruments GmbH, Munich). The quantity of lysine formed was determined using an amino acid analyzer from Eppendorf-BioTronik (Hamburg, Germany) by ion exchange chromatography and post-column derivation with ninhydrin detection. Table 1 shows the result of the test.

TABLE 1

| Strain | OD | Lysine HCl |
| --- | --- | --- |
| DSM5715 | 7.9 | 13.53 |
| DSM5715Δlrp | 7.8 | 14.27 |

The abbreviations and names are defined as follows. The lengths stated should be considered to be approximate.

| | |
| --- | --- |
| sacB: | sacB gene |
| oriV: | replication origin V |
| KmR: | kanamycin resistance |
| XmaI | restriction site of the restriction enzyme XmaI |
| XbaI | restriction site of the restriction enzyme XbaI |
| Δlrp: | incomplete fragment of the lrp gene with internal 380 bp deletion |

What is claimed is:

1. An isolated nucleic acid comprising a nucleotide sequence selected from the group consisting of:
   (a) the nucleotide sequence as set forth in SEQ ID NO:1; and
   (b) a nucleotide sequence fully complementary to (a).

2. A vector comprising the nucleic acid of claim 1.

3. A bacterial host cell comprising the vector of claim 2.

4. The bacterial host cell of claim 3 wherein said host cell is of the species *Escherichia coli*.

* * * * *

SEQUENCE LISTING

```
<160> NUMBER OF SEQ ID NOS: 9

<210> SEQ ID NO 1
<211> LENGTH: 715
<212> TYPE: DNA
<213> ORGANISM: Corynebacterium glutamicum
<220> FEATURE:
<221> NAME/KEY: CDS
<222> LOCATION: (151)..(612)
<223> OTHER INFORMATION: lrp-Gen
<220> FEATURE:
<221> NAME/KEY: -10_signal
<222> LOCATION: (88)..(93)
<223> OTHER INFORMATION:
```

```
<220> FEATURE:
<221> NAME/KEY: -35_signal
<222> LOCATION: (62)..(67)
<223> OTHER INFORMATION:

<400> SEQUENCE: 1
gccgataacc tttatcatct ggttccaggg ctgccttgga tggcgacacc tccaggcttg      60
aatgaatctc ttgcgttttt tgcacactac aatcatcaca caattgccgg gtagttttgt    120
tgccagtttg cgcacctcaa ctaggctatt gtg caa tat atg aag cta gat tcc    174
                                  Met Gln Tyr Met Lys Leu Asp Ser
                                    1               5 att gat cgc gca att att gcg gag ctt agc gcg aat gcg cgc atc tca      222
Ile Asp Arg Ala Ile Ile Ala Glu Leu Ser Ala Asn Ala Arg Ile Ser
     10                  15                  20 aat ctc gca ctg gct gac aag gtg cat ctc act ccg gga cct tgc ttg      270
Asn Leu Ala Leu Ala Asp Lys Val His Leu Thr Pro Gly Pro Cys Leu
 25                  30                  35                  40 agg agg gtg cag cgt ttg gaa gcc gaa gga atc att ttg ggc tac agc      318
Arg Arg Val Gln Arg Leu Glu Ala Glu Gly Ile Ile Leu Gly Tyr Ser
                 45                  50                  55 gcg gac att cac cct gcg gtg atg aat cgt gga ttt gag gtg acc gtg      366
Ala Asp Ile His Pro Ala Val Met Asn Arg Gly Phe Glu Val Thr Val
             60                  65                  70 gat gtc act ctc agc aac ttc gac cgc tcc act gta gac aat ttt gaa      414
Asp Val Thr Leu Ser Asn Phe Asp Arg Ser Thr Val Asp Asn Phe Glu
         75                  80                  85 agc tcc gtt gcg cag cat gat gaa gta ctg gag ttg cac agg ctt ttt      462
Ser Ser Val Ala Gln His Asp Glu Val Leu Glu Leu His Arg Leu Phe
 90                  95                 100 ggt tcg cca gat tat ttt gtc cgc atc ggc gtt gct gat ttg gag gcg      510
Gly Ser Pro Asp Tyr Phe Val Arg Ile Gly Val Ala Asp Leu Glu Ala
105                 110                 115                 120 tat gag caa ttt tta tcc agt cac att caa acc gtg cca gga att gca      558
Tyr Glu Gln Phe Leu Ser Ser His Ile Gln Thr Val Pro Gly Ile Ala
                125                 130                 135 aag atc tca tca cgt ttt gct atg aaa gtg gtg aaa cca gct cgc ccc      606
Lys Ile Ser Ser Arg Phe Ala Met Lys Val Val Lys Pro Ala Arg Pro
            140                 145                 150 cag gtg tgaagcatgc attttgaagc atgaatcttt tcatctagt gaaggactga        662
Gln Val tcccatgcgt atgaaatcaa tcgcagcaat tgcaatcgct accgccgccc tgg           715

<210> SEQ ID NO 2
<211> LENGTH: 154
<212> TYPE: PRT
<213> ORGANISM: Corynebacterium glutamicum

<400> SEQUENCE: 2

Met Gln Tyr Met Lys Leu Asp Ser Ile Asp Arg Ala Ile Ile Ala Glu
 1               5                  10                  15

Leu Ser Ala Asn Ala Arg Ile Ser Asn Leu Ala Leu Ala Asp Lys Val
                 20                  25                  30

His Leu Thr Pro Gly Pro Cys Leu Arg Arg Val Gln Arg Leu Glu Ala
             35                  40                  45

Glu Gly Ile Ile Leu Gly Tyr Ser Ala Asp Ile His Pro Ala Val Met
         50                  55                  60

Asn Arg Gly Phe Glu Val Thr Val Asp Val Thr Leu Ser Asn Phe Asp
 65                  70                  75                  80
```

-continued

Arg Ser Thr Val Asp Asn Phe Glu Ser Ser Val Ala Gln His Asp Glu
            85                  90                  95

Val Leu Glu Leu His Arg Leu Phe Gly Ser Pro Asp Tyr Phe Val Arg
            100                 105                 110

Ile Gly Val Ala Asp Leu Glu Ala Tyr Glu Gln Phe Leu Ser Ser His
            115                 120                 125

Ile Gln Thr Val Pro Gly Ile Ala Lys Ile Ser Ser Arg Phe Ala Met
    130                 135                 140

Lys Val Val Lys Pro Ala Arg Pro Gln Val
145                 150

<210> SEQ ID NO 3
<211> LENGTH: 19
<212> TYPE: DNA
<213> ORGANISM: Corynebacterium glutamicum
<220> FEATURE:
<221> NAME/KEY: misc_feature
<222> LOCATION: (1)..(19)
<223> OTHER INFORMATION: Primer lrp_up_for

<400> SEQUENCE: 3
ggcgcccggg ggcgtgcgc                                            19

<210> SEQ ID NO 4
<211> LENGTH: 48
<212> TYPE: DNA
<213> ORGANISM: Artificial Sequence
<220> FEATURE:
<221> NAME/KEY: misc_feature
<222> LOCATION: (1)..(48)
<223> OTHER INFORMATION: Primer lrp_up_rev

<400> SEQUENCE: 4
cccatccact aaacttaaac aaatggaatc tagcttcata tattgcac            48

<210> SEQ ID NO 5
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: Primer lrp_do_for

<400> SEQUENCE: 5
tgtttaagtt tagtggatgg ggctatgaaa gtggtgaaac cagct               45

<210> SEQ ID NO 6
<211> LENGTH: 24
<212> TYPE: DNA
<213> ORGANISM: Corynebacterium glutamicum
<220> FEATURE:
<221> NAME/KEY: misc_feature
<222> LOCATION: (1)..(24)
<223> OTHER INFORMATION: Primer lrp_do_rev

<400> SEQUENCE: 6
ccggtctaga ggatccgcaa ttcc                                      24

<210> SEQ ID NO 7
<211> LENGTH: 397
<212> TYPE: DNA
<213> ORGANISM: Corynebacterium glutamicum
<220> FEATURE:
<221> NAME/KEY: misc_feature
<222> LOCATION: (1)..(397)

<223> OTHER INFORMATION: lrp part 1

<400> SEQUENCE: 7

| | | | | | |
|---|---|---|---|---|---|
| ggcgcccggg | ggcgtgcgcc | cacaacgagg | gcgatgacca | gcatttcggt | ggagcccgcg | 60 |
| aaaatcaggc | cggaaaacag | tggggctgcc | caccattcgt | agccgtattg | aataaccaag | 120 |
| agaccaaacg | caataccaat | cgggtacatg | cccaaacctg | cagcaaggga | ggttttttaga | 180 |
| ccttgcgcga | tttcgtagcg | ccgataacct | ttatcatctg | gttccagggc | tgccttggat | 240 |
| ggcgacacct | ccaggcttga | atgaatctct | tgcgtttttt | gcacactaca | atcatcacac | 300 |
| aattgccggg | tagttttgtt | gccagtttgc | gcacctcaac | taggctattg | tgcaatatat | 360 |
| gaagctagat | tccatttgtt | taagtttagt | ggatggg | | | 397 |

<210> SEQ ID NO 8
<211> LENGTH: 402
<212> TYPE: DNA
<213> ORGANISM: Corynebacterium glutamicum
<220> FEATURE:
<221> NAME/KEY: misc_feature
<222> LOCATION: (1)..(402)
<223> OTHER INFORMATION: lrp part 2

<400> SEQUENCE: 8

| | | | | | |
|---|---|---|---|---|---|
| tgtttaagtt | tagtggatgg | ggctatgaaa | gtggtgaaac | cagctcgccc | ccaggtgtga | 60 |
| agcatgcatt | ttgaagcatg | aatctttttc | atctagtgaa | ggactgatcc | catgcgtatg | 120 |
| aaatcaatcg | cagcaattgc | aatcgctacc | gccgccctgg | ctggtggcac | tggagtcgct | 180 |
| agcgcacagg | aagctggctc | gactgctggt | tcctccaacc | tcagctctgg | gatccagctt | 240 |
| ccacaagaag | ccaccgatct | gttgagcttc | ctgcctgctg | ctcaggctgc | gcaggttgaa | 300 |
| ggagcaattc | agagcaccgc | tggtttcttt | gccgttggac | tcggctcgac | cgccattggt | 360 |
| tccactgcag | tgaccttggg | aattgcggat | cctctagacc | gg | | 402 |

<210> SEQ ID NO 9
<211> LENGTH: 778
<212> TYPE: DNA
<213> ORGANISM: Artificial Sequence
<220> FEATURE:
<221> NAME/KEY: misc_feature
<222> LOCATION: (1)..(349)
<223> OTHER INFORMATION: upsream region of the lrp gene
<220> FEATURE:
<221> NAME/KEY: misc_feature
<222> LOCATION: (350)..(376)
<223> OTHER INFORMATION: 5'-region of the lrp-Gens
<220> FEATURE:
<221> NAME/KEY: misc_feature
<222> LOCATION: (377)..(397)
<223> OTHER INFORMATION: 21 bp extension
<220> FEATURE:
<221> NAME/KEY: misc_feature
<222> LOCATION: (398)..(433)
<223> OTHER INFORMATION: 3'-region of the lrp gene
<220> FEATURE:
<221> NAME/KEY: misc_feature
<222> LOCATION: (434)..(778)
<223> OTHER INFORMATION: downstream region of the lrp gene

<400> SEQUENCE: 9

| | | | | | |
|---|---|---|---|---|---|
| ggcgcccggg | ggcgtgcgcc | cacaacgagg | gcgatgacca | gcatttcggt | ggagcccgcg | 60 |
| aaaatcaggc | cggaaaacag | tggggctgcc | caccattcgt | agccgtattg | aataaccaag | 120 |
| agaccaaacg | caataccaat | cgggtacatg | cccaaacctg | cagcaaggga | ggttttttaga | 180 |
| ccttgcgcga | tttcgtagcg | ccgataacct | ttatcatctg | gttccagggc | tgccttggat | 240 |

```
ggcgacacct ccaggcttga atgaatctct tgcgtttttt gcacactaca atcatcacac    300
aattgccggg tagttttgtt gccagtttgc gcacctcaac taggctattg tgcaatatat    360
gaagctagat tccatttgtt taagtttagt ggatggggct atgaaagtgg tgaaaccagc    420
tcgcccccag gtgtgaagca tgcattttga agcatgaatc tttttcatct agtgaaggac    480
tgatcccatg cgtatgaaat caatcgcagc aattgcaatc gctaccgccg ccctggctgg    540
tggcactgga gtcgctagcg cacaggaagc tggctcgact gctggttcct ccaacctcag    600
ctctgggatc cagcttccac aagaagccac cgatctgttg agcttcctgc ctgctgctca    660
ggctgcgcag gttgaaggag caattcagag caccgctggt ttctttgccg ttggactcgg    720
ctcgaccgcc attggttcca ctgcagtgac cttgggaatt gcggatcctc tagaccgg     778
```